US009773097B2

(12) United States Patent
Mu et al.

(10) Patent No.: US 9,773,097 B2
(45) Date of Patent: Sep. 26, 2017

(54) SYSTEM AND METHOD OF OPTIMIZING BLENDING RATIOS FOR PRODUCING PRODUCT

(71) Applicant: YOKOGAWA ELECTRIC CORPORATION, Musashino-shi, Tokyo (JP)

(72) Inventors: Sheng Jing Mu, Singapore (SG); Dan Zeng, Singapore (SG); Wen Hua Wang, Singapore (SG); Jin Sheng Gu, Singapore (SG)

(73) Assignee: Yokogawa Electric Corporation, Tokyo (JP)

( * ) Notice: Subject to any disclaimer, the term of this patent is extended or adjusted under 35 U.S.C. 154(b) by 495 days.

(21) Appl. No.: 14/453,140

(22) Filed: Aug. 6, 2014

(65) Prior Publication Data
US 2016/0042074 A1  Feb. 11, 2016

(51) Int. Cl.
G06F 7/00 (2006.01)
G06F 17/30 (2006.01)
G06F 19/00 (2011.01)

(52) U.S. Cl.
CPC .................. *G06F 19/70* (2013.01)

(58) Field of Classification Search
CPC ................ G06F 17/30867; G06F 17/30469
USPC .......................................... 707/710
See application file for complete search history.

(56) References Cited

U.S. PATENT DOCUMENTS

| | | | |
|---|---|---|---|
| 6,214,241 B1* | 4/2001 | Miura | B01D 61/04 210/753 |
| 6,403,748 B1* | 6/2002 | Powers | B01F 5/241 525/53 |
| 6,476,158 B1* | 11/2002 | England | C08L 67/02 524/537 |
| 9,080,111 B1* | 7/2015 | Huff | C10G 29/205 |
| 2004/0220902 A1* | 11/2004 | Gates | G06F 17/30864 |
| 2005/0223633 A1* | 10/2005 | Sankaranarayanan | G05D 11/139 44/629 |
| 2006/0287980 A1* | 12/2006 | Liu | G06F 17/30864 |
| 2007/0014185 A1* | 1/2007 | Diosse | B01F 5/241 366/9 |
| 2007/0023323 A1* | 2/2007 | Van Den Berg | C10G 45/58 208/114 |
| 2007/0208677 A1* | 9/2007 | Goldberg | G06N 7/005 706/13 |
| 2008/0005118 A1* | 1/2008 | Shakib | G06F 17/30864 |
| 2008/0167742 A1* | 7/2008 | Endo | G02B 5/0242 700/97 |
| 2009/0171813 A1* | 7/2009 | Byrne | G06F 17/30867 705/26.1 |
| 2010/0007924 A1* | 1/2010 | Matsuzaki | H04N 1/40012 358/3.24 |
| 2010/0063332 A1* | 3/2010 | Chang | C07C 29/095 568/852 |

(Continued)

*Primary Examiner* — Binh V Ho
(74) *Attorney, Agent, or Firm* — Sughrue Mion, PLLC

(57) ABSTRACT

An optimization system includes a) one or more processors; b) a loop search engine configured to perform a loop search based on a random blending ratio of blending components for at least a product, and to generate a first optimized blending ratio; and c) a local search engine configured to perform a local search based on the first optimized blending ratio, and to generate a second optimized blending ratio. The loop search engine and the local search engine are implemented on the one or more processors.

29 Claims, 5 Drawing Sheets

(56) References Cited

U.S. PATENT DOCUMENTS

| | | | | |
|---|---|---|---|---|
| 2010/0257171 | A1* | 10/2010 | Shekhawat | G06F 17/30707 707/738 |
| 2012/0116841 | A1* | 5/2012 | Bippert | G06Q 30/0202 705/7.31 |
| 2012/0279114 | A1* | 11/2012 | Kelly | C10L 1/023 44/451 |
| 2012/0296690 | A1* | 11/2012 | Varvarezos | G06Q 10/08 705/7.26 |
| 2014/0075831 | A1* | 3/2014 | Kelly | C10L 1/023 44/451 |
| 2014/0149393 | A1* | 5/2014 | Bhatt | G06F 17/30867 707/722 |
| 2014/0324813 | A1* | 10/2014 | Mathur | G06F 17/3053 707/707 |

* cited by examiner

SYSTEM AND METHOD OF OPTIMIZING BLENDING RATIOS FOR PRODUCING PRODUCT

BACKGROUND OF THE INVENTION

Field of the Invention

This disclosure generally relates to a system and a method of optimizing blending ratios for producing distinct products.

Backgrounds

Blending oils, including both crude oil and product oil, is made for refinery operations. Due to the large volume of each oil product that is formed, it can be in some cases desirable to blend the product, for example, gasoline or diesel, at the lowest possible cost, while satisfying quality specifications. For example, if gasoline blends are not made at the smallest possible deviations from the specifications, the refinery profit can be impacted significantly.

Crude oil refineries will produce various liquid fuels by blending intermediate product streams in a manner which minimizes use of more valuable components, while meeting the product specifications. Product specifications either are greater than or less than or equal to constraints for various product properties or qualities. Examples of the product properties or qualities may include, but are not limited to, octane number, Reid vapour pressure, sulphur content, specific gravity, etc. The blending rules of fuel oil are well known in the art. The goal of blending operations has been to meet product demand and specifications and only as a by-product to minimize give-away losses, that is, losses that occur when a premium quality product must be sold at regular product prices.

SUMMARY

In one embodiment, an optimization system may include, but is not limited to, a) one or more processors; b) a loop search engine configured to perform a loop search based on a random blending ratio of blending components for at least a product, and to generate a first optimized blending ratio; and c) a local search engine configured to perform a local search based on the first optimized blending ratio, and to generate a second optimized blending ratio, wherein the loop search engine and the local search engine are implemented on the one or more processors.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE EMBODIMENTS

Before describing some embodiments, the following matters will be explained, in order to facilitate the understanding of the embodiments.

Figure 1:
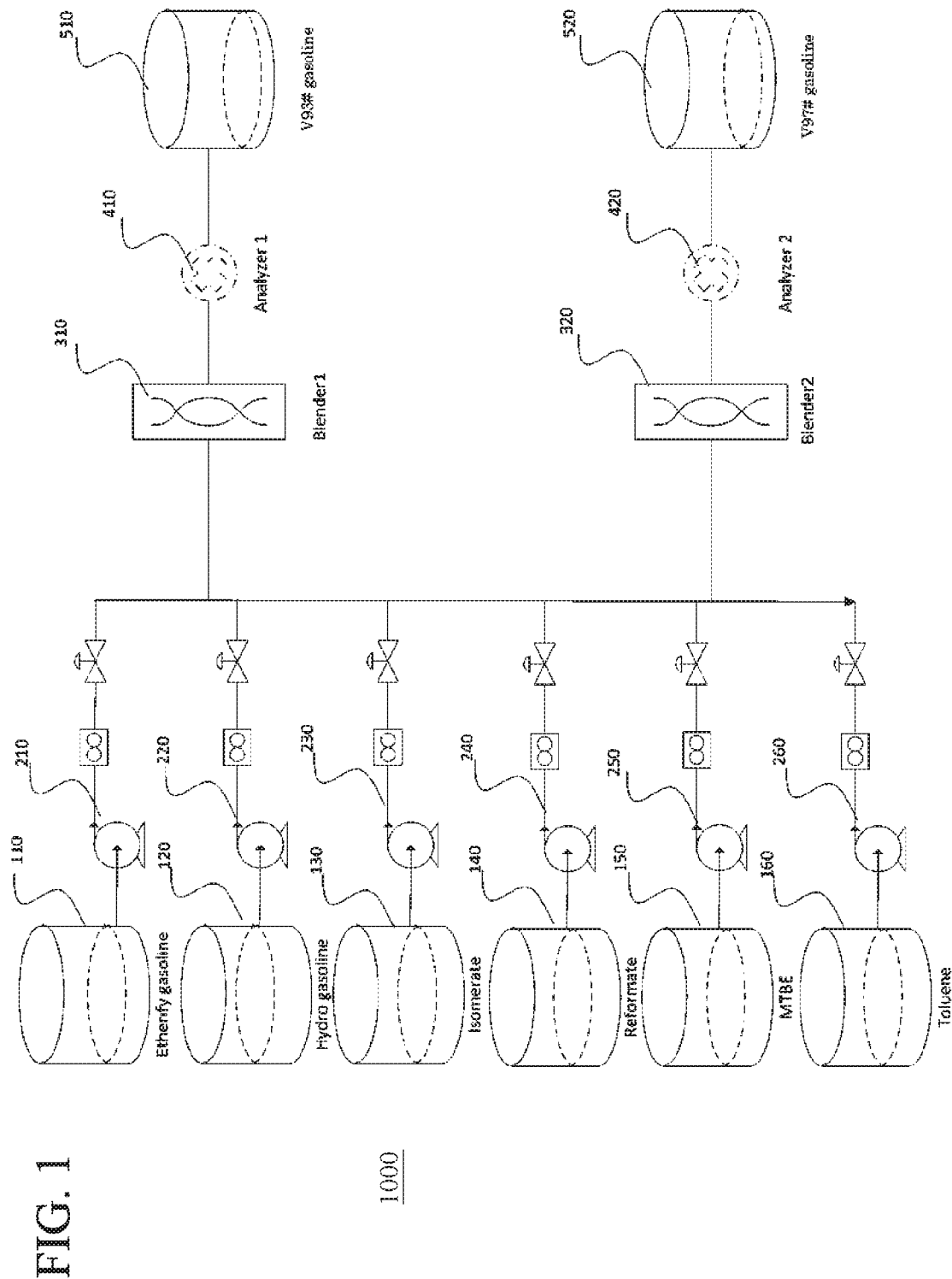
FIG. 1 is a diagram of an example of a system for producing gasoline of different qualities in some embodiments of the present invention.

A typical example of the related art of a system for crude oil refinery will hereinafter be described to facilitate the understanding of the embodiments. The system is configured to blend a plurality of different oil blend components. The system includes plural component tanks and one or more blenders as shown in FIG. 1. Different oil blend components are stored separately in the different component tanks. The different oil blend components are fed separately from the different component tanks to the blender for blending the different oil blend components. Blending the oil blend components is carried out at a predetermined ratio known as a blend recipe in order to meet the specifications for a final oil product. In some cases, various grades of gasoline can be blended. In a case that the system includes a plurality of blenders, the system may be designed so that the blenders can operate in parallel. To meet a contracted product demand, an optimal refinery operation is to meet contracted products while minimizing operating costs and inventory carrying costs.

Usually, there is one blender for each type of liquid products, i.e. one blender for a gasoline, one blender for diesel, etc. Refineries operate to meet the contracted product demand. Hence, an optimal refinery operation is one that meets contracted products lifting while minimizing operating costs and inventory carrying costs. The blend components arrive from upstream process units and are stored in their respective tanks. In the blend headers so called to as blenders, the blend components are mixed in a predetermined ratio such as the blend recipe to meet the specifications for different gasoline grades that is being blended. There can be one or more blenders operating in parallel.

Currently, many plants use manually set component ratios for blending and experienced blend rules for quality prediction. However, these often give rise to target product quality off-specification or over specification, leading to additional costs associated with re-blending and excessive use of high-cost blend components. In particular, users tend to use spreadsheets to calculate blending recipes manually. Typically, such a spreadsheet is designed with proper format and built with blend rules. The blend rules for product oil such as gasoline are compliance to the Standard Test Method ASTM, including Reid Vapor Pressure (RVP), Motor Octane Number (MON), Research Octane Number (RON), flash point, etc. Users specify the component oil property in the component tank and tank heel property in the product tank, and key in the recipe ratio of each component for blending. The spreadsheet can then be used to calculate the predicted property of product oil accordingly. In this way, users will carry out a trial and error process by adjusting the blending ratio and checking the predicted property of product oil until it is close to the target, for instance, product oil being on specification. The effectiveness of adjusting component ratios thus depends on the experience of the user. Less experienced users may spend a few hours or more to achieve the blending recipe on specification. Highly experienced users may take a shorter time to have an acceptable blending recipe on specification. However, even though a user can eventually arrive at a reasonable blending recipe with a certain amount of effort using the spreadsheet method, this recipe can be different from the optimal or most beneficial one, in terms of operation cost, maximum consumption of certain component oil, or other optimal targets that plant operators may be interested in.

Currently many plants use manually set component ratio for blending, and using experienced blend rule for quality prediction, which cause the target product quality off-specification or over specification, and then results in re-blending and/or high component cost. Recipe optimization system of some embodiments will allow user to foresee the quality of target product by utilizing the component property, blending ratio, heel product in target tank and dedicate oil blending rules, and then to further optimize the component blending ratio according to specified optimization target. Furthermore, as compared with other optimization method used for oil blending, which is reply on a given set of initial recipe ratio, Recipe optimization system of some embodiments will provide a global optimization method for oil blending that without any human interruption of providing the initial recipe ratio, by using hybrid Genetic algorithms search method.

Genetic algorithms (GAs) are intelligent stochastic methods, inspired by the Darwinian natural evolution principle of "survival of the fittest". GA defines a genetic representation of the solution domain characterized by a fitness function. A standard evolution proceeds in cycles of initialization, selection and reproduction until termination conditions have been reached. Standard Genetic algorithms (Standard GA) are expected to have good global search capability and to be able to overcome potential barriers. In some complicated cases, the standard GA can become trapped in local potential wells (premature convergence).

In some embodiments, a genetic algorithm (GA) loop search coupled with a local search scheme to overcome the problems mentioned last. The Nelder-Mead (NM) simplex method, which is derivative-free local search, is incorporated into the hybrid GA loop search procedure and form the global optimization search scheme. The Genetic algorithm (GA) loop search is executed to keep the improvement of the best solution as a whole generation, while the Nelder-Mead (NM) simplex search is to further refine the individual solution of the whole generation. The Genetic algorithm (GA) loop search is used to maximize the fitness value of the population, while the Nelder-Mead (NM) simplex search is used to fine-tune the solutions of each generation, as well as to prune the search space for the Genetic algorithm (GA) loop search.

In one embodiment, an optimization system may include, but is not limited to, a) one or more processors; b) a loop search engine configured to perform a loop search based on a random blending ratio of blending components for at least a product, and to generate a first optimized blending ratio; and c) a local search engine configured to perform a local search based on the first optimized blending ratio, and to generate a second optimized blending ratio, wherein the loop search engine and the local search engine are implemented on the one or more processors.

In some cases, the loop search engine and the local search engine may be configured to reiterate the loop search and the local search cyclically.

In the above cases, the loop search may include, but is not limited to, a genetic algorithm loop search, and the local search may include, but is not limited to, a Nelder-Mead simplex method search.

In some cases, the optimization system may further include, but is not limited to, d) a generation counter module configured to count a generation number every time the loop search engine and the local search engine have performed the loop search and the local search, respectively. The generation counter module may be implemented on the one or more processors. The loop search engine and the local search engine may be configured to reiterate the loop search and the local search cyclically until the generation number counted by the generation counter module reaches a predetermined number. The loop search may include, but is not limited to, a genetic algorithm loop search. The local search may further include, but is not limited to, a Nelder-Mead simplex method search.

In some cases, the optimization system may further include, but is not limited to, e) an initialization module configured to create the random blending ratio automatically, wherein the initialization module is implemented on the one or more processors.

In the last-mentioned cases, the initialization module may be configured to create the random blending ratio, based on at least: an optimization target; configuration parameters of the loop search and the local search; and a set of boundary conditions.

In the last-mentioned cases, the set of boundary conditions may include, but is not limited to: a specification of a product, the product being a blend of a plurality of blending components; an available amount of each of the blending components; and relevant properties of each of the blending components.

In the last-mentioned cases, the specification of the product may include at least one of sulfur content, research octane number, motor octane number, Reid vapour pressure, flash point, viscosity, olefin, benzene, oxygen, aromatics, boiling point, true specific gravity, and price of each product.

In the last-mentioned cases, the relevant properties may include at least one of: sulfur content, research octane number, motor octane number, Reid vapour pressure, flash point, viscosity, olefin, benzene, oxygen, aromatics, boiling point, true specific gravity, and cost of each of the blending components.

In the above-mentioned cases, the optimization target may include an optimization of an objective function configured to: reduce a total cost of all the blending components to be used; increase a total profit of all the products together; reduce a total remaining mass balance of each blending component; and increase throughput of at least one of the products.

In some cases, the optimization system may further include, but is not limited to, f) a user interface configured to display the second optimized blending ratio on a display screen.

In the last-mentioned cases, the user interface is configured to receive to entry of at least: an optimization target; configuration parameters of the loop search and the local search; and a set of boundary conditions.

In the last-mentioned cases, the optimization system may further include, but is not limited to, e) an initialization module configured to create the random blending ratio based on at least: the optimization target, the configuration parameters of the loop search and the local search, and the set of boundary conditions.

In the last-mentioned cases, the set of boundary conditions may include, but is not limited to, a specification of a product which is a blend of a plurality of blending components; an available amount of each of the blending components; and relevant properties of each of the blending components.

In the last-mentioned cases, the optimization target may include an optimization of an objective function configured to: reduce a total cost of all the blending components to be used; increase a total profit of all the products together; reduce a total remaining mass balance of each blending component; and increase throughput of at least one of the products.

In the above-mentioned cases, the user interface is configured to receive an entry of information of an existing volume of each product in its product tank.

In some cases, the loop search engine may include, but is not limited to, a genetic algorithm loop search engine. The local search engine may include, but is not limited to a Nelder-Mead simplex method search engine.

In some cases, the optimization system may further include, but is not limited to, g) a memory device accessible by the one or more processor, the memory device stores a set of program components that, when executed by the one or more processor, cause the processor to act as the loop search and the local search engine.

In the last-mentioned cases, the memory device stores: a set of information. The set of information may include, but is not limited to, a plurality of predefined boundary conditions; a plurality of minimized objective functions; a plurality of maximized objective functions, which are the reciprocals of the minimized objective functions; and a plurality of configuration parameters for a genetic algorithm loop search and a Nelder-Mead simplex method for the loop search and the local search engine, respectively.

In some cases, the one or more processor may be programmed to implement the loop search engine and the local search engine.

In another embodiment, a method of optimizing a blending ratio of blending components for at least a product may include, but is not limited to, a) performing a loop search based on a random blending ratio of blending components for at least a product, to generate a first optimized blending ratio; and b) performing a local search based on the first optimized blending ratio, to generate a second optimized blending ratio. The loop search and the local search are performed using one or more processors.

In some cases, the method may further include, but is not limited to, c) reiterating the loop search and the local search cyclically.

In the last-mentioned cases, the loop search may include, but is not limited to, a genetic algorithm loop search. The local search may include, but is not limited to, a Nelder-Mead simplex method search.

In some cases, the method may further include, but is not limited to, d) counting a generation number every time the loop search and the local search have been performed, wherein the counting operation is implemented using the one or more processors; and e) reiterating the loop search and the local search cyclically until the generation number counted reaches a predetermined number. The loop search may include, but is not limited to, a genetic algorithm loop search. The local search may include, but is not limited to, a Nelder-Mead simplex method search.

In some cases, the method may further include, but is not limited to, 0 creating the random blending ratio, based on at least: an optimization target; configuration parameters for the loop search and the local search; and a set of boundary conditions. The set of boundary conditions may include, but is not limited to, a specification of a product, the product being a blend of a plurality of blending components; an available amount of each of the blending components; and relevant properties of each of the blending components.

In still another embodiment, a non-transitory computer-readable storage medium stores a set of information. The set of information may include, but is not limited to, a plurality of predefined boundary conditions; a plurality of minimized objective functions; a plurality of maximized objective functions, which are the reciprocals of the minimized objective functions; and a plurality of configuration parameters for a genetic algorithm loop search and a Nelder-Mead simplex method.

In some cases, the plurality of predefined boundary conditions may include, but is not limited to a plurality of predefined oil blending rules; a plurality of configurable number of component tank and product tank; a plurality of configurable minimum and maximum values of blending ratio parameters; a plurality of configurable minimum and maximum values of product oil property specifications; a plurality of configurable minimum and maximum values of volumes of component tank and product tank; a plurality of configurable remaining volume of product tank; a plurality of configurable cost of component oil and price of product oil; and a plurality of configurable penalty coefficients for constraints to get constraint conditions as constraint violation term.

An article of manufacture including a computer-readable medium having instructions stored thereon that, when executed by a computing device, cause said computing device to perform operations which may include, but is not limited to, a) performing a loop search based on a random blending ratio of blending components for at least a product, to generate a first optimized blending ratio; and b) performing a local search based on the first optimized blending ratio, to generate a second optimized blending ratio.

A method of creating a random blending ratio for optimizing a blending ratio of blending components for at least a product may include, but is not limited to, a) receiving, by one or more processors, entry of at least a-1) an optimization target, a-2) configuration parameters for a loop search and a local search, and a-3) a set of boundary conditions which are stored on a non-transitory computer-readable storage medium; and b) creating, by the one or more processors, a random blending ratio based on at least the optimization target, the configuration parameters, and the set of boundary conditions.

In some cases, the set of boundary conditions may include, but is not limited to, a specification of a product, the product being a blend of a plurality of blending components; an available amount of each of the blending components; and relevant properties of each of the blending components.

In some cases, the optimization target may include an optimization of an objective function configured to: reduce a total cost of all the blending components to be used; increase a total profit of all the products together; reduce a total remaining mass balance of each blending component; and increase throughput of at least one of the products.

[Overall of System and Method]

Some embodiments of the system and method are directed to the blending optimization, to find optimal blend recipes that change significantly less often than in the current practice, thereby leading to a large reduction in execution time and operation cost. Some embodiments of the system and method can be used for optimizing blend recipes alone or in combination with predicting the quality of target products for process industrial plants, including tank farm and terminal operations' management.

In some embodiments, a recipe optimizer can be used alone as an off-line blending calculator for predicting quality of a target product. Typical examples of the target product may include, but are not limited to, target or final oil products such as gasoline, diesel, fuel oil, etc. and then optimizing the blending recipe for process industrial plants, including tank farm and terminal operations' management. In some embodiments, the recipe optimizer can use hybrid genetic algorithms (HGA) as the global optimization solver to optimize the product oil blending recipe without requiring entering an initial recipe ratio. In some cases, the recipe optimization formulation can be formed by using oil blending property rules and mass balance rules as constraints and a set of optimization targets to realize different optimal targets, such as operation costs and execution times. The recipe optimizer is a system which can support both in-line blending and batch blending.

Some embodiments of the recipe optimization system will allow users to foresee or predict the quality of each target product by utilizing the component property, blending ratio, heel product in target tank and follow oil blending rules, and then to further optimize the component blending ratio according to specified optimization targets. Furthermore, compared with other optimization method used for oil blending, which rely on a given set of initial recipe ratios, some embodiments will provide a global optimization method for oil blending by using a hybrid genetic algorithm search method that does not require any human input to provide the initial recipe ratio.

Genetic algorithms (GAs) are intelligent stochastic methods, inspired by the Darwinian natural evolution principle of "survival of the fittest". The GA defines a genetic representation of the solution domain characterized by a fitness function. A standard evolution proceeds in cycles of initialization, selection and reproduction until termination conditions have been reached. Standard GA is expected to have good global search capability and to be able to overcome potential barriers. However, in some complicated cases, the standard GA can become trapped in local potential wells, or premature convergence. In some embodiments, a genetic algorithm (GA) loop search coupled with a local search scheme can be used to overcome this issue. In some embodiments, the Nelder-Mead (NM) simplex method, which is a derivative-free local search, is incorporated into the genetic algorithm (GA) loop search procedure to form a global optimization or hybrid GA search scheme. The GA search is executed to keep the improvement of the best solution as a whole generation, while the NM simplex method is to further refine the individual solution of the whole generation. The GA can be used to maximize the fitness value of the population, while the NM simplex search can be used to fine-tune the solutions of each generation, as well as to prune the search space for the GA loop search. Some embodiments of the system, method and optimizer can be realized by combining a standard real-coded genetic algorithm (SRCGA) with the NM simplex method as a hybrid GA method to search the solution with the highest fitness value in the generated population database. The standard GA search procedures, which may include, but are not limited to, selection, crossover and mutation, are first performed, and then followed by the local optimization procedure, the NM simplex method. By applying this method, the blending optimization search can guarantee global optimization within the search space with high convergence efficiency.

Recipe optimizer is off-line blending calculator which is used for predicting quality of target product oil, such as gasoline, diesel, fuel oil, etc. and then optimizing the blending recipe for process industrial plants, including tank farm and terminal operations' management. Some embodiments provide hybrid genetic algorithms (HGA) as the global optimization solver to optimize the product oil blending recipe without entry the initial recipe ratio. In particularly, the recipe optimization formulation is formed by the oil blending property rules and mass balance rules as the constraints and a set of optimization targets to realize different optimal targets, such as operation cost and execution time. Recipe optimizer is a system which can support both in-line blending and batch blending.

Embodiments of oil blending optimization will be now described herein with reference to illustrative drawings. Those skilled in the art will recognize that many alternative embodiments can be accomplished using the teaching of the embodiments of the present invention and that the invention is not limited to the embodiments illustrated for explanatory purpose.

[Overall of Oil Production System]

FIG. 1 is a diagram of an example of a system for producing gasoline #93 and gasoline #97. The component oils used for blending are etherified light gasoline, catalytic hydrogenation heavy gasoline, isomerate, reformate, MTBE and toluene.

The gasoline blending system 1000 includes first to sixth tanks 110, 120, 130, 140, 150, and 160, first to sixth feeders 210, 220, 230, 240, 250, and 260, first and second blenders 310, 320, first and second analyzers 410 and 420, and first and second final product tanks 510 and 520. The first tank 110 is provided for storing an etherified light gasoline. The second tank 120 is provided for storing a catalytic hydrogenation heavy gasoline. The third tank 130 is provided for storing an isomerate. The fourth tank 140 is provided for storing a reformate. The fifth tank 150 is provided for storing an MTBE. The sixth tank 160 is provided for storing toluene. The first final product tank 510 is provided for storing a gasoline #93. The second final product tank 520 is provided for storing a gasoline #97. The first blender 310 and the first analyzer 410 are provided for producing the gasoline #93. The second blender 320 and the second analyzer 420 are provided for producing the gasoline #97.

The first feeder 210 is configured to communicate between the first tank 110 for storing the etherified light gasoline, and the first blender 310 for producing the gasoline #93. The first feeder 210 feeds a controlled amount of the etherified light gasoline to the first blender 310. The first feeder 210 is also configured to communicate between the first tank 110 for storing the etherified light gasoline, and the second blender 320 for producing the gasoline #97. The first feeder 210 feeds a controlled amount of the etherified light gasoline to the second blender 320. The first feeder 210 may include a pump, a flow meter and a valve for feeding the etherified light gasoline at a controlled flow rate or a controlled amount to the first blender 310 or the second blender 320 from the first tank 110.

The second feeder 220 is configured to communicate between the second tank 120 for storing the catalytic hydrogenation heavy gasoline, and the first blender 310 for producing the gasoline #93. The second feeder 220 feeds a controlled amount of the catalytic hydrogenation heavy gasoline to the first blender 310. The second feeder 220 is also configured to communicate between the second tank 120 for storing the catalytic hydrogenation heavy gasoline, and the second blender 320 for producing the gasoline #97. The second feeder 220 feeds a controlled amount of the catalytic hydrogenation heavy gasoline to the second blender 320. The second feeder 220 may include a pump, a flow meter and a valve for feeding the catalytic hydrogenation heavy gasoline at a controlled flow rate or a controlled amount to the first blender 310 or the second blender 320 from the second tank 120.

The third feeder 230 is configured to communicate between the third tank 130 for storing the isomerate and the first blender 310 for producing the gasoline #93. The third feeder 230 feeds a controlled amount of the isomerate to the first blender 310. The third feeder 230 is also configured to communicate between the third tank 130 for storing the isomerate and the second blender 320 for producing the gasoline #97. The third feeder 230 feeds a controlled amount of the isomerate to the second blender 320. The third feeder 230 may include a pump, a flow meter and a valve for feeding the isomerate at a controlled flow rate or a controlled amount to the first blender 310 or the second blender 320 from the third tank 130.

The fourth feeder 240 is configured to communicate between the fourth tank 140 for storing the reformate and the first blender 310 for producing the gasoline #93. The fourth feeder 240 feeds a controlled amount of the reformate to the first blender 310. The fourth feeder 240 is also configured to communicate between the fourth tank 140 for storing the reformate and the second blender 320 for producing the gasoline #97. The fourth feeder 240 feeds a controlled amount of the reformate to the second blender 320. The fourth feeder 240 may include a pump, a flow meter and a valve for feeding the reformate at a controlled flow rate or a controlled amount to the first blender 310 or the second blender 320 from the fourth tank 140.

The fifth feeder 250 is configured to communicate between the fifth tank 150 for storing the MTBE and the first blender 310 for producing the gasoline #93. The fifth feeder 250 feeds a controlled amount of the MTBE to the first blender 310. The fifth feeder 250 is also configured to communicate between the fifth tank 150 for storing the MTBE and the second blender 320 for producing the gasoline #97. The fifth feeder 250 feeds a controlled amount of the MTBE to the second blender 320. The fifth feeder 250 may include a pump, a flow meter and a valve for feeding the MTBE at a controlled flow rate or a controlled amount to the first blender 310 or the second blender 320 from the fifth tank 150.

The sixth feeder 260 is configured to communicate between the sixth tank 160 for storing the toluene and the first blender 310 for producing the gasoline #93. The sixth feeder 260 feeds a controlled amount of the toluene to the first blender 310. The sixth feeder 260 is also configured to communicate between the sixth tank 160 for storing the toluene and the second blender 320 for producing the gasoline #97. The sixth feeder 260 feeds a controlled amount of the toluene to the second blender 320. The sixth feeder 260 may include a pump, a flow meter and a valve for feeding the toluene at a controlled flow rate or a controlled amount to the first blender 310 or the second blender 320 from the sixth tank 160.

The first blender 310 is configured to receive a controlled amount of the etherified light gasoline through the first feeder 210 from the first tank 110. The first blender 310 is configured to receive a controlled amount of the catalytic hydrogenation heavy gasoline through the second feeder 220 from the second tank 120. The first blender 310 is configured to receive a controlled amount of the isomerate through the third feeder 230 from the third tank 130. The first blender 310 is configured to receive a controlled amount of the reformate through the fourth feeder 240 from the fourth tank 140. The first blender 310 is configured to receive a controlled amount of the MTBE through the fifth feeder 250 from the fifth tank 150. The first blender 310 is configured to receive a controlled amount of toluene through the sixth feeder 260 from the sixth tank 160.

Based on a first optimized oil blending recipe for producing the gasoline #93, there are determined the flow rates or controlled amounts of feedings of the etherified light gasoline, the catalytic hydrogenation heavy gasoline, the isomerate, the reformate, the MTBE and toluene from the first to sixth tanks 110, 120, 130, 140, 150 and 160 to the first blender 310. The first blender 310 is configured to blend the etherified light gasoline, the catalytic hydrogenation heavy gasoline, the isomerate, the reformate, the MTBE and toluene at the first blending ratio in accordance with the first optimized oil blending recipe for producing the gasoline #93. The first optimized oil blending recipe has been prepared by the recipe optimizer described above. The first blender 310 performs the blending to produce the gasoline #93 which is then fed through the first analyzer 410 to the first final product tank 510. The first blender 310 has a blending process controller BPC and a distributed control system DCS to adjust each of the first to sixth flow rates of the first to sixth feeders 210, 220, 230, 240, 250 and 260 in accordance with the first optimized oil blending recipe for producing the gasoline #93. The first analyzer 410 may be designed to work with the blending process controller and the distributed control system of the first blender 310 to adjust each of the first to sixth flow rates of the first to sixth feeders 210, 220, 230, 240, 250 and 260 for producing the gasoline #93.

Based on a second optimized oil blending recipe for producing the gasoline #97, there are determined the flow rates or controlled amounts of feedings of the etherified light gasoline, the catalytic hydrogenation heavy gasoline, the isomerate, the reformate, the MTBE and toluene from the first to sixth tanks 110, 120, 130, 140, 150 and 160 to the second blender 320. The second blender 320 is configured to blend the etherified light gasoline, the catalytic hydrogenation heavy gasoline, the isomerate, the reformate, the MTBE and toluene at a second blending ratio in accordance with a second optimized oil blending recipe for producing the gasoline #97. The second optimized oil blending recipe has been prepared by the recipe optimizer described above. The second blender 320 performs the blending to produce the gasoline #97 which is then fed through the second analyzer 420 to the second final product tank 520. The second blender 320 also has a blending process controller BPC and a distributed control system DCS to adjust each of the first to sixth flow rates of the first to sixth feeders 210, 220, 230, 240, 250 and 260 in accordance with the second optimized oil blending recipe for producing the gasoline #97. The second analyzer 420 may be designed to work with the blending process controller and the distributed control system of the second blender 320 to adjust each of the first to sixth flow rates of the first to sixth feeders 210, 220, 230, 240, 250 and 260 for producing the gasoline #97.

[Examples of Global Recipe Optimization]

Figure 2:
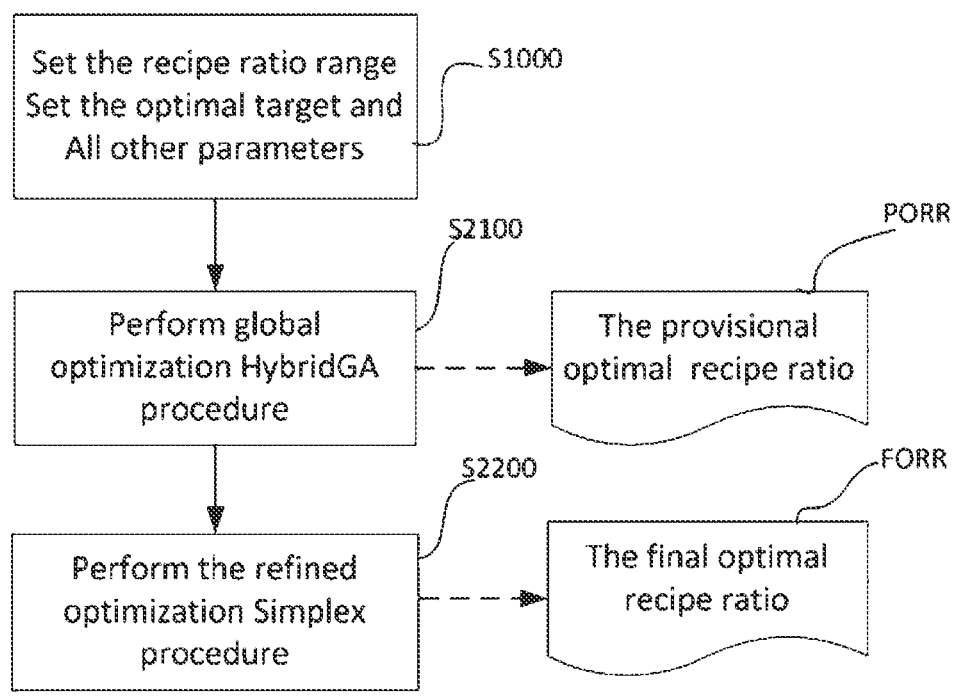
FIG. 2 is a flow chart of a hybrid recipe optimization for preparing an optimized oil blending recipe for producing a gasoline as a final product in some embodiments of the present invention.

FIG. 2 is a flow chart of a hybrid recipe optimization for preparing an optimized oil blending recipe for producing a gasoline as a final product. The hybrid recipe optimization includes two basic steps. The first basic step is a global optimization to find a provisional set of optimal recipe ratios. The second basic step is a local optimization to refine the provisional set of optimal recipe ratios and obtain the final set of the refined optimal recipe ratios.

In Step S1000, there are input and initialization steps, including setting a recipe ratio range, the optimal target and other parameters and creating a random solution pool.

In Step S2100, the recipe optimizer performs a global optimization process using genetic algorithm as a solver with reference to the recipe ratio range, the optimal target and other parameters, to generate a provisional set of optimal recipe ratios PORR.

In Step S2200, the recipe optimizer performs a local optimization process using Simplex method, to refine the provisional set of optimal recipe ratios and obtain the final set of the refined optimal recipe ratios.

Figure 3:
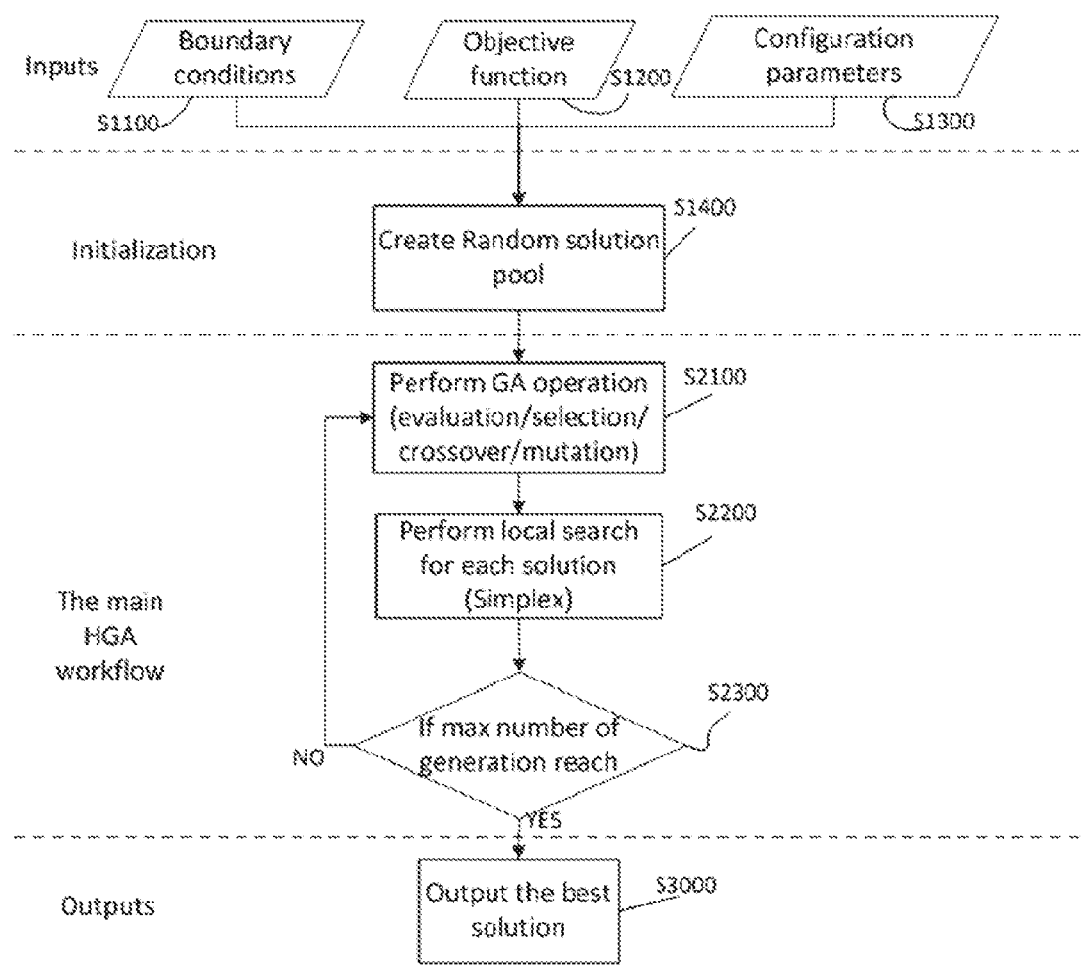
FIG. 3 is a flow chart of hybrid genetic algorithms (HGA) of a recipe optimizer in some embodiments of the present invention.

FIG. 3 is a flow chart of hybrid genetic algorithms (HGA). The hybrid genetic algorithms (HGA) include four layers 1) input layer, 2) initialization layer, 3) hybrid genetic algorithms layer, and 4) output layer.

The first layer is the input layer. The input layer includes the following three steps S1100, S1200, and S1300. In step S1100, these inputs may be made either manually or the recipe optimization (RO) reads the inputs from OPC/historian or other data sources. In either cases, the recipe optimizer acquires boundary conditions or upper and lower limits of acceptable ranges of the recipe ratios for hybrid genetic algorithms (HGA) procedure. In step S1200, the specified objective function can be provided by user selection from a list of objective functions, such as maximize product profits, minimize the total cost, minimize the remain component volume, etc. The recipe optimizer acquires specified objective functions for hybrid genetic algorithms (HGA) procedure. In step S1300, the configuration parameters for hybrid genetic algorithms (HGA) procedure may include two parts, parameters for genetic algorithms GA and parameters for simplex method. The parameters for genetic algorithms GA may include the maximum generation number, the population number, the crossover and mutation probability, etc. The parameters for simplex method may include the convergence tolerance, the search range, the maximum number of iteration, etc. The recipe optimizer acquires configuration parameters for hybrid genetic algorithms (HGA) procedure. In the recipe optimization (RO) context, the boundary conditions include the upper limit and the lower limit of the acceptable ranges in volumes of the feed tanks and the final product tanks, the upper limit and the lower limit of the acceptable ranges of product oil properties such as RON, MON, Density, and RVP.

The second layer is the initialization layer. The initialization layer includes the following step S1400. In step S1400, the recipe optimizer creates random solution pool. The initialization layer is to generate the initial population by randomly distributing the solution within the predefined upper and lower limits of the acceptable ranges. For example, the recipe optimizer may be configured to randomly distribute the solutions within the predefined upper and lower limits of the acceptable ranges.

The third layer is the hybrid genetic algorithm procedural layer. The hybrid genetic algorithm procedural layer includes the following steps S2100, S2200 and S2300. In step S2100, the recipe optimizer performs the genetic algorithm (GA) operation using the random solution pool or the previous generation. The genetic algorithm (GA) may include evaluation and selection of the solution according to an initial fitness value, and then perform crossover and mutation operation, to mimic the evolution process of organism population. A new generation will be created after the genetic algorithm GA procedure, which, in general, has higher fitness capability or improved performance, compared with the previous generation. In step S2200, the recipe optimizer performs the local optimization procedure using a Simplex method for refinement of each solution from the genetic algorithm GA. Each member of new generation will be further refined by simplex method, a local optimization procedure, to speed up the evolution process. The Simplex method is driven by the minimum of objective function, using the reversed function of the genetic algorithm GA fitness value calculation function. In step S2300, the recipe optimizer determines if the generation reaches the maximum number of the generation. If not yet, in step S2100 the recipe optimizer will perform the genetic algorithm GA procedure again to create a newer generation which, in general, has higher fitness capability or further improved performance, compared with the previous generation. The recipe optimizer will continue the loop of the genetic algorithm GA operation in step S2100 and the Simplex method in step S2200 to create the next generation until the number of the generation reaches the maximum generation number. Finally the recipe optimizer will generate the best solution with the highest possible fitness value.

The fourth layer is the output layer. The output layer includes the step S3000. In step S3000, the recipe optimizer outputs the best solution with the highest possible fitness value as the global optimization solution, or the provisional optimized recipe ratio set-point value for each feed tank to respective product tank, in this recipe optimization context.

Figure 4:
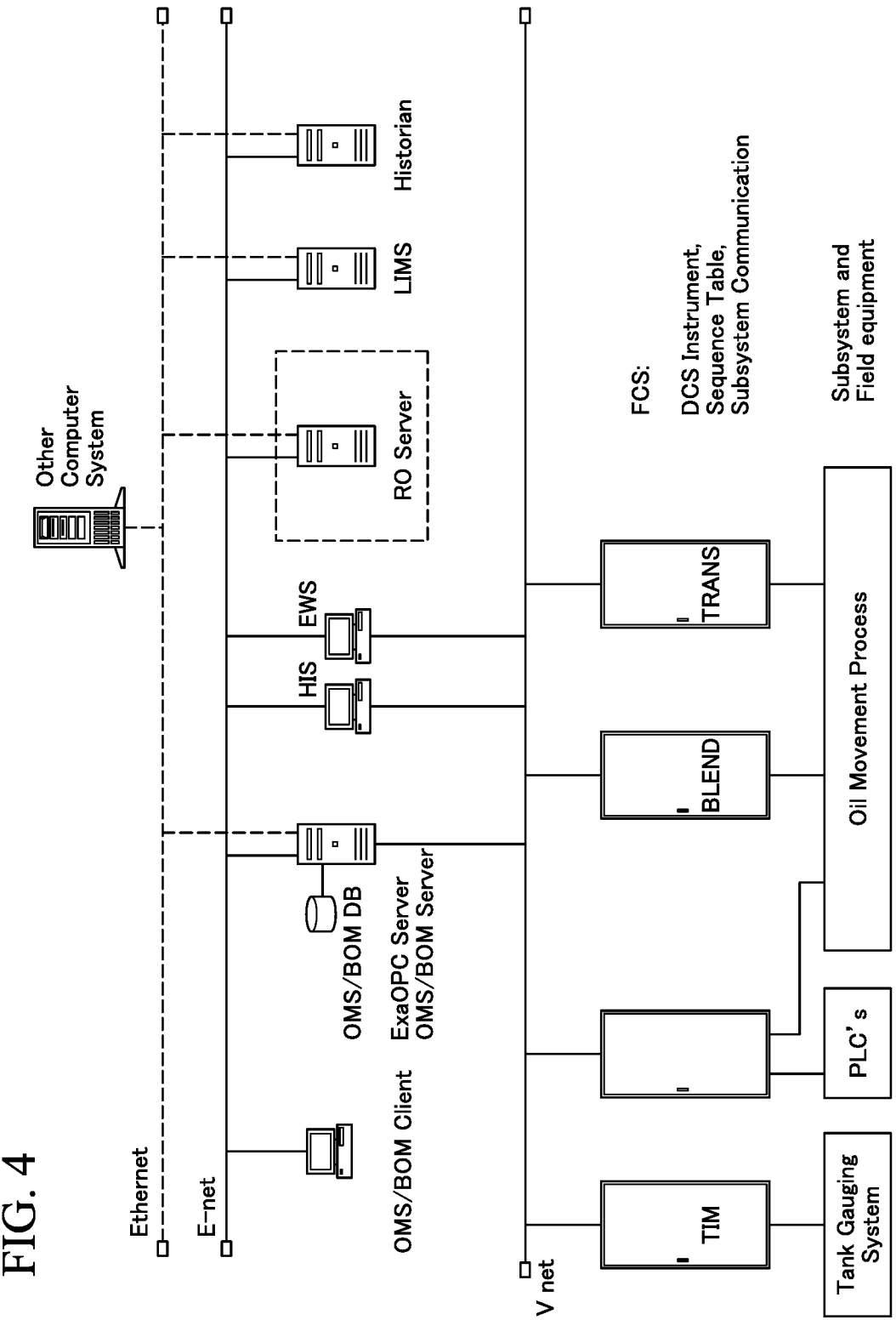
FIG. 4 is a diagram of an example of a typical integrated solution system configuration for process industries oil movement system with recipe optimizer server in some embodiments of the present invention.
Figure 5:
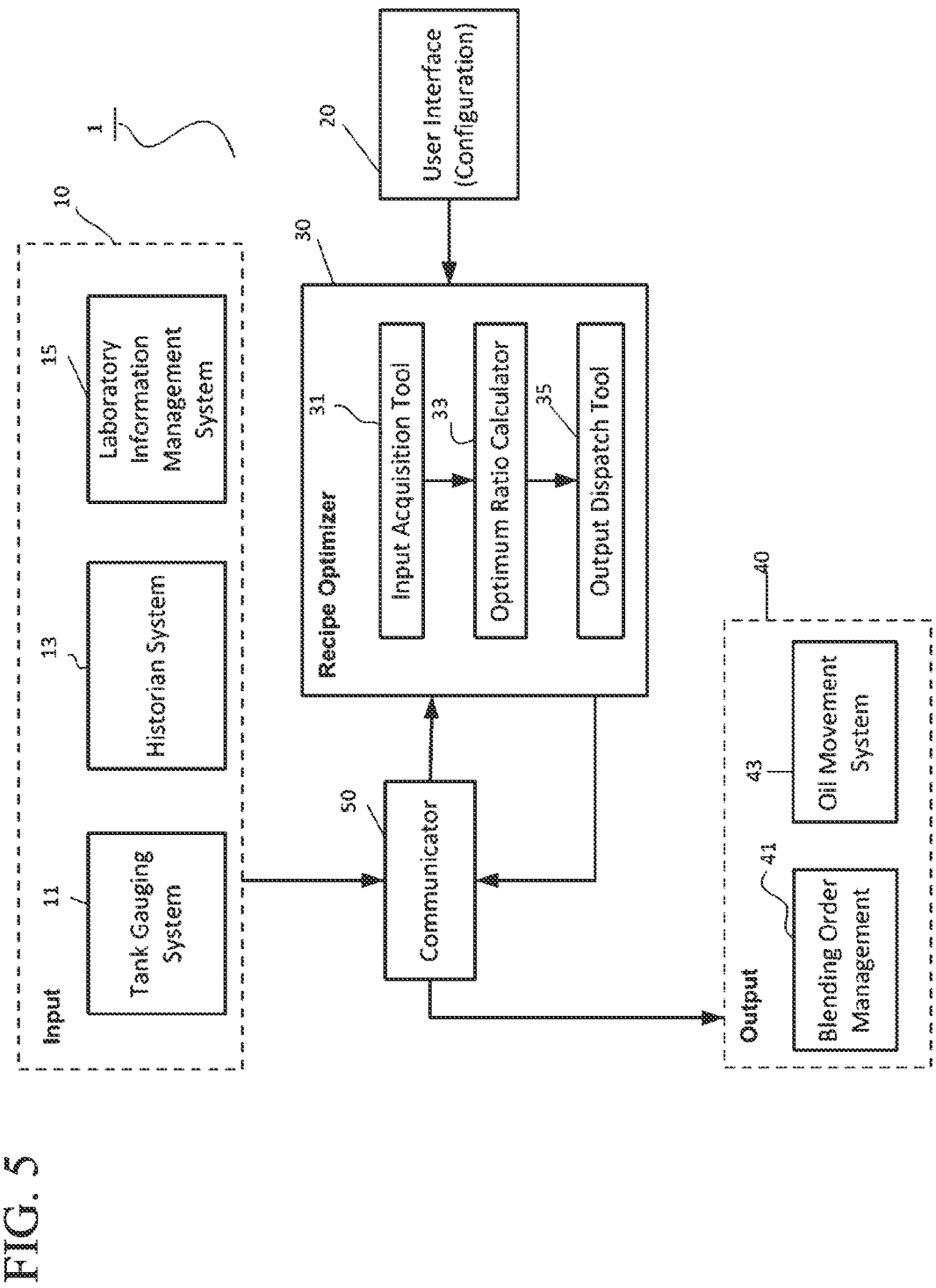
FIG. 5 is a block diagram of functional blocks of the system configuration of FIG. 4.

FIG. 4 is a diagram of an example of a typical integrated solution system configuration for process industries oil movement system with recipe optimizer server. FIG. 5 is a block diagram of functional blocks of the system configuration of FIG. 4. A recipe optimization system 1 may include, but is not limited to, an input module 10, a user interface 20, a recipe optimizer 30, an output module 40 and a communicator 50.

The input module 10 includes a tank gauging system 11, a historian system 13, and a laboratory information management system 15. The user interface 20 can be used to configure the recipe optimizer 30. The recipe optimizer 30 includes an input acquisition tool 31, an optimum ratio calculator 33, and an output dispatch tool 35. The input acquisition tool 31 is configured to acquire inputs supplied from the input module 10 through the communicator 50. The input acquisition tool 31 in FIG. 5 corresponds to the input layer in FIG. 3. The optimum ratio calculator 33 performs the step S1400 to create random solution pool and is configured to calculate the optimum ratios of blending components to produce the final product. The optimum ratio calculator 33 in FIG. 5 corresponds to the initialization layer and the hybrid genetic algorithm procedural layer, including the steps S2100, S2200 and S2300 of FIG. 3. The loop of the genetic algorithm (GA) operation and the local optimization procedure using the Simplex method will be continued until the number of the generation reaches the maximum generation number, thereby generating the best solution with the highest possible fitness value. The output dispatch tool 35 is configured to output the best solution with the highest possible fitness value which is then supplied through the communicator 50 to the output module 40. The output dispatch tool 35 in FIG. 5 corresponds to the output layer, including the step S3000, in which the best solution with the highest possible fitness value is output as the global optimization solution. The output module 40 includes a BOM (Blending Order Management) 41, and an OMS (Oil Movement System) 43.

This system configuration is to provide an integrated blending operation solution for refinery plants and terminals. System components associated with the recipe optimization (RO) package are stored in the recipe optimization (RO) server. Namely, the recipe optimization (RO) server includes the recipe optimization (RO) program package and one or more processors to execute the recipe optimization (RO) program, and also a database. The optimization of recipe is also executed in this server.

The inputs of the recipe optimization (RO) system are receiving information from different systems include the LIMS, the historian, and the tank gauging system. Particularly, the lab quality analysis results of both component tank and the product tank heel oil quality should be from the LIMS at the beginning of each blending batch cycle or in fixed frequency for continuous process. The component tank volume and product tank heel volume should be either from the historian or tank gauging system directly at the beginning of each blending batch cycle or in fixed frequency for continuous process. The communication between each system could be through OPC (OLE for process control) client or flat file exchange in the agreed format. The other information of the recipe optimization (RO) system such as the tank capacity, different limitations, optimization target, product oil quality specification, etc. should be defined in the recipe optimization RO server by a system user using the user interface 20. The outputs of the recipe optimization (RO) system, including the best recipe ratio and rate from each component tank to each product tank, the optimized target value, the predicted product oil quality, would be displayed in the recipe optimization (RO) server monitor, and the instructions of the recommended recipe ratio could be downloaded to the OMS/BOM for implementation at the beginning of each blending batch cycle or in fixed frequency for continuous process.

A plurality of predefined boundary conditions may for example include, but is not limited to the followings: 1) a plurality of predefined oil blending rules; 2) a plurality of configurable number of component tank and product tank; 3) a plurality of configurable minimum and maximum value of blending ratio parameters; 4) a plurality of configurable minimum and maximum value of product oil property specifications; 5) a plurality of configurable minimum and maximum value of the component tank and product tank volumes; 6) a plurality of configurable remaining volume of product tank; 7) a plurality of configurable cost of component oil and price of product oil; and 8) a plurality of configurable penalty coefficients for the constraints to get the constraint conditions as constraint violation term.

A plurality of objective functions for selection are predefined under Yokogawa proprietary: 1) a plurality of predefined minimized objective function by including both the original objective function and constraint violation term; 2) a plurality of predefined maximized objective function, which is the reciprocal of the minimized objective function; and 3) a plurality of configuration parameters for application in generic algorithm and NM simplex methods to realize the satisfied performance in terms of accurate optimal search and practical computation loading.

The vector solution is the blending recipe ratio parameter for at least two component tanks and at least one product tank.

The initialization includes the random distribution for each vector solution; each vector solution has multiple parameters of blending recipe ration, by, for each parameter, assigning a random value between its minimum and maximum value as initial start point of this parameter, using the size of population, and assigning random values for size of population.

The genetic algorithms (GA) operation procedure includes evaluation, selection, crossover, and mutation processes in these order.

The evaluation process includes evaluating the genetic algorithms (GA) fitness value of each vector solution by calculating the predefined maximized objective function for each vector solution. The genetic algorithms (GA) fitness value should be greater or equal to zero.

The selection process includes using the genetic algorithms GA fitness value to obtain the best fit and selecting vector solutions through a weighted roulette wheel procedure, where higher fit vector solutions are allocated more space on the wheel and hence are more likely to be selected. The roulette wheel space is allocated according to a vector solution rank within the population list. The selected vector solution would be chosen for the following crossover and mutation operations. The operation of elite set, a subset highest fitness value of the population, is maintained in the genetic algorithms GA procedure, which is not allowed to die or be mutated.

The crossover process includes using the probabilities of crossover, for example, 0.9, for 90% of the vector solutions in the whole population for each two vector solutions, generating a new vector solutions using below arithmetic crossover operation formula ($\alpha$ is a random value from 0 to 1). New vector solutions X' are created by favorably selecting two parent vector solutions $X_1$ and $X_2$ creating new vector solutions by mixing the parent vector solution's parameters. The fitness value of newly generated vector solution X' will be compared with those of the two parent vector solutions $X_1$ and $X_2$ and the vector solution with higher fitness value will remain in the population. In this way, the whole population size remains unchanged:

$$X'=\alpha*X_1+(1-\alpha)*X_2$$

The mutation process includes using the probabilities of mutation, for example, 0.05, for 5% of the vector solutions in the whole population, for each vector, and changing at least one parameter. To maintain the population diversity, a vector solution parameter is randomly changed by non-uniform mutation operator:

$$X'_k = \begin{cases} X_k + \Delta(t, UB - X_k), & \text{if a random } \beta < 0.5 \\ X_k - \Delta(t, UB - X_k), & \text{if a random } \beta \geq 0.5 \end{cases}$$

where LB and UB are the lower and upper bounds of the variables $X_k$, t is the current generation number, $\beta$ is the random number from 0.1.

The function $\Delta(t,y)$ is calculated by:

$$\Delta(t,y)=y \cdot (1-r^{(1-t/T)^b})$$

where r is a uniform random number from [0, 1], T is the maximal generation number [max number of generation=40], and b is a system parameter determining the degree of dependency on the iteration number [the degree of dependency on the iteration number=1].

The fitness value of new generated vector solution $X'_k$ will be compared with that of the existing vector solutions $X_k$ and the vector solution with higher fitness value will be remained in the population. In this way, the whole population size is remained the same.

The local search is performed, for each vector solution after performing the genetic algorithms GA procedure, by running the Nelder-Mead simplex function minimization procedure to find an optimized vector solution within its local range. The objective function used in the NM simplex function minimization procedure is the predefined minimized objective function. The NM simplex function includes the iteration of steps of ordering, centroid and transformation. The operations in the transformation step include reflect, expand, contract and shrink.

Predefined configuration parameters are used for: 1) defining initial simplex extend size using the step size of the initial simplex; 2) defining the termination limit by checking the variance of the objective function improvement during the iteration using the terminating tolerance for the variance of function values; and 3) defining the maximum number of simplex step iteration reached using the maximum number of function evaluations.

After the local search procedure is performed, the generation number t will be compared with the maximum generation number T. If the generation number t reaches the maximum number of generation T, then the whole optimization program will stop and output the final result, which the vector solution with the highest fitness value among the final generation's population. If the generation number t does not yet reach the maximum number of generation T, then the program will go back to the genetic algorithms GA operation procedure to continue the iteration of the hybrid genetic algorithms GA program.

[Examples of Oil Blending Optimization]

An example of the method for optimization for blending ratios for blending oil components to produce a final oil product will be described with reference to an exemplary simplified scenario with the blending of two oil products gasoline #93 and gasoline #97, as shown on Table 1. The component oils used for blending gasoline #93 and gasoline #97 are Etherified Light Gasoline, Catalytic hydrogenation heavy gasoline, Isomerate, Reformate, MTBE and Toluene, as shown on Table 4. Properties of the oil products as a result of blending include laboratory test parameters such as sulfur content, Research Octane Number (RON), Olefin (OLV), Benzene (BNZ), Oxygen (OXY) and Aromatics (ARO). It should be that in a real situation, the actual blend recipe may have more components and properties.

The following is an explanation of the symbols used in the expressions below:
m: the number of components, in this case 6
n: the number of blend lines, in this case 2
l: the number of properties, in this case 6
i=1, 2, 3, 4 . . . m: Component tanks 1, 2, . . . m.
j=1, 2, . . . n: Product lines 1, 2 . . . n.
$V_{Rj}$: Remaining Volume of product tank j before blending.
$V_{ij}$: Volume from component tank i to product tank j.
$V_j$: Final volume of product tank j after blending.
$V_i^{LB}$: Low total volume limit of component tank i.
$V_i^{HB}$: High total volume limit of component tank i.
$C_i$: Cost of component in tank i. For example, US$1400/MT.
$P_j$: Price of final product in tank j after blending. For example, US$1880/MT.
$PR_{ik}$, k=1, 2, 3 . . . l, i=1, 2, . . . m: the value of property k in components tank i.
$PR_{Rjk}$, k=1, 2, 3 . . . l, j=1, 2, . . . n: the value of property k in product tank j before blending.
$PR_{jk}$, k=1, 2, 3, . . . l, j=1, 2, . . . n: the value of property k in product tank j after blending.
$PR_{jk}^{LB}$, k=1, 2, 3 . . . l, j=1, 2, . . . n: low limit of property k in product tank j specification.
$PR_{jk}^{HB}$, k=1, 2, 3 . . . l, j=1, 2, . . . n: low limit of property k in product tank j specification.
$G_k$, k=1, 2, . . . l: the giveaway cost of property k.
X=[$V_{11}$, $V_{21}$, $V_{31}$, $V_{41}$, $V_{51}$, $V_{61}$, $V_{12}$, $V_{22}$, $V_{32}$, $V_{42}$, $V_{52}$, $V_{62}$]: a vector solution.

The below blend rules are used in this example:
Blend Rule 1 for RON:

$$TN = \frac{1}{(1 + \exp(-b*(MON - m)))}$$

where h=0.05594, m=102.94.
The component TN values blend linearly by volume. The blend TN is converted back to RON using the same formulae.
Blend Rule 2 for Sulfur:
Linear by Weight, $PR_{j\ Sulfur} = \Sigma(WeightRatio_{ij} * PR_{i\ Sulfur})$
Where $WeightRatio_{ij} = VolRatio_{ij} * Density_i / Density_j$
Blend Rule 3 for OLV/BZN/OXY/ARO:
Linear by Volume, $PR_{jk} = \Sigma(VolRatio_{ij} * PR_{ik})$
Where k is one of the properties, OLV, BZN, OXY or ARO.

There are four objective functions to be optimized in this example, as described below:
A. Minimize Total Cost of Components:

In order to calculate a total cost of the components used in blending each oil product, relative cost for each component should be input before optimization. The cost of each component is maintained in a component master database. In order to get a minimum total cost of the components, the formula (1) below needs to be minimized:

$$\min f(V_{ij}) = \sum_{i=1}^{m} C_i \sum_{j=1}^{2} V_{ij} \tag{1}$$

B. Maximize Total Profit of all Blend Lines

In order to get a maximum profit of all the blending lines with a limited inventory of the components, a user can optimize the blending to get maximum profit based on the cost of each component and the product price of each oil product from the blending lines. To maximize total profit, the formula (2) below needs to be optimized:

$$\max f(V_{ij}) = \sum_{j=1}^{2}\left(P_j V_j - \sum_{i=1}^{m} C_i \sum_{j=1}^{2} V_{ij}, \right. \tag{2}$$

j = specified blend line number

C. Minimize Total Remaining Component Mass Balance
A user can seek to get a minimum total remaining mass balance for the components. To do so, the formula (3) below needs to be optimized:

$$\min f(V_{ij}) = \sum_{i=1}^{m}\left(V_{Ri} - \sum_{i=1}^{m} V_{ij}\right) \tag{3}$$

D. Maximize Throughput of Specified Blend Line
A user can assign which blend line will deliver a maximum amount of product. This formula is used for getting maximum profit a blend product. To do so, the formula (4) below needs to be optimized:

$$\min f(V_{ij}) = V_j, f = \text{specified blend line number} \tag{4}$$

In the method, all the optimization formulae described above need to meet the following three groups of constraints:
1. Final Product Property Must Meet Product Specification:
$PR_{jk}^{LB} \leq PR_{jk} \leq PR_{jk}^{HB}$, j=1, 2, . . . n, k=1, 2, . . . 1
2. Total Volume of Consumed Component Must be in Specified Range:
$V_i^{LB} \leq \Sigma_{j=1}^n V_{ij} \leq V_i^{HB}$, i=1, 2, . . . m
3. Mass Balance of Component Consumed and Product Produced in the Overall Plant:

In the method, a user enters certain required inputs into an input module of a computer implemented recipe optimization program that is configured to perform the optimization. The inputs of the method 100 comprise three parts, as described below:

[Constraints that Form Boundary Conditions for the Optimization]

Constraints that form boundary conditions for the optimization are to ensure that the optimal recipe meets all product specifications and available component amounts for blending by considering the component properties, product tank heel volume (amount of product left in the product tank) and properties, etc. In this example, the following boundary condition inputs are required:

a. Product Specification:

A user should define the boundary of each property for each product, such as 93.2<RON<93.5, Sulfur<10 ppm for #93 gasoline. An example is given in Table 1 below.

TABLE 1

BLENDING PRODUCT QUALITY SPECIFICATION

| No. | Product | Sulfur, ppm | RON | OLV, v % | BNZ, v % | OXY, wt % | ARO, v % |
|---|---|---|---|---|---|---|---|
| 1 | V93# gasoline | <10 | >93.2 | <18.00 | <1 | <2.7 | <35 |
| 2 | V97# gasoline | <10 | >97.2 | <18.00 | <1 | <2.7 | <35 | b. Component Inventory:

An available amount of each component for blending the products should be provided. The final component consumption should not exceed the inventory of this component. An example is shown in Table 2 below, where the inventory of each component is given in kTon.

TABLE 2

BLENDING COMPONENT INVENTORIES AND PROPERTIES

| No. | Blending Component | Inventory, k Ton | Sulfur, ppm | RON | OLV, v % | BNZ, v % | OXY, wt % | ARO, v % | density, g/cm3 |
|---|---|---|---|---|---|---|---|---|---|
| 1 | Etherified Light Gasoline | 80.55 | 34 | 95 | 45.20% | 0.70% | 2.7% | 1.60% | 0.699 |
| 2 | Catalytic Hydrogenation Heavy Gasoline | 57.77 | 10 | 95 | 14.30% | 0.40% | 2.7% | 51.10% | 0.805 |
| 3 | Isomerate | 75.62 | 0.5 | 83.9 | 0 | 0 | 0 | 0 | 0.6412 |
| 4 | Reformate | 36.71 | 3 | 110 | 0 | 0 | 0 | 80.00% | 0.874 |
| 5 | MTBE | 13.38 | 5 | 117 | 0.19% | 0 | 18.20% | 0 | 0.7405 |
| 6 | Toluene | 10 | 2 | 115 | 0 | 0.05% | 0 | 100.00% | 0.866 | c. Component Property and Heel Information:

Product property after blending is predicted based on the component properties as exemplified in Table 2 above, product heel volume and component blend volume/ratio.

The blending profit and cost calculation rely on the prices of each component and product.

Optimization Targets:

Based on the real situations or requirements, a user should choose one out of the four objective functions described above to be the target of recipe optimization. In this example, the objective function C, Minimize Total Remaining Component Mass Balance, is chosen.

Configuration Parameters for Hybrid GA Method:

The parameters for hybrid GA, including both for standard GA and NM simplex method should be provided as inputs in the method 100. An exemplary set of inputs is shown in Table 3 below. The parameters for standard GA include the population size, the maximum number of generations, the probabilities of crossover and mutation operations, and the degree of dependency on the iteration number. The population size depends on the number of parameter in the solution. Normally, 10*Number of parameter is recommended as the population size; a total population size of no greater than 200 is advised due to performance issues.

The maximum number of generations depends on the complexity of the problem. For the oil blending optimization problem that involves only a few exponential nonlinear blending rules, 40-50 generations of iteration is sufficient for the hybrid genetic algorithm. Also, the number of generations relates to the population size and the maximum number of NM simplex function evaluations. Larger population sizes or a bigger number of NM simplex function evaluations could improve the hybrid GA search efficiency and then request smaller number of GA generation.

It is known that crossover operations should cover most of the solution while mutation operations should happen for only few solutions, to stabilize the characteristics of the whole population. Therefore, the probabilities of crossover should approach 1.0 and the probabilities of mutation should approach 0.0, respectively. The degree of dependency on the iteration number is a system parameter determining the degree of dependency on the iteration number in the non-uniform mutation operator. This parameter is used to guide the mutation operation to generate the mutated generation in the space uniformly initially (when generation is small), and very locally at later generation.

The parameters for NM simplex method include the step size of the initial simplex, the terminating tolerance for the variance of function values and the maximum number of function evaluations. The recommended parameters value for the step size of the initial simplex depends on the size of the solution space. The value may need to be large if the space is wide. Normally, 1~2 is a recommended step size of the initial simplex. The terminating tolerance for the variance of function value depends on the numeric degree of the objective function. Small tolerance data for an objective function having a small value is recommended to avoid premature termination of the search. The maximum number of NM simplex function evaluations serves a similar function as the terminating tolerance. In the NM simplex method integrated with the GA method, a small number of function evaluations, such as 10-20, is advised to slightly improve the GA population. An exemplary set of input parameters is shown in Table 3 below.

TABLE 3

THE CONFIGURATION PARAMETERS OF HGA

| No. | Parameter | Input Value |
|---|---|---|
| 1 | the size of population | 200 |
| 2 | the maximum number of generation | 40 |
| 3 | the probabilities of crossover | 0.9 |
| 4 | the probabilities of mutation | 0.05 |
| 5 | the degree of dependency on the iteration number | 1 |
| 6 | the step size of the initial simplex | 2 |
| 7 | the terminating tolerance for the variance of function values | 0.001 |
| 8 | the maximum number of NM simplex function evaluation | 10 |

Outputs of the recipe optimization program of the method include the following three parts, 1) blending ratio of each component tank to each product tank, 2) predicted profit/cost of blending operation or the optimized target value, and 3) predicted properties of products after blending.

1) Blending Ratio of Each Component Tank to Each Product Tank:

A comparison of the blending ratio results with and without using the recipe optimization (RO) in accordance with the method is shown in Table 4 below.

TABLE 4

| | | Without RO | With RO |
|---|---|---|---|
| | Total Remaining Component Mass Balance | 37.00, m³ | 35.60, m³ |
| V93# Gasoline | Etherify Gasoline (v %) | 19.64% | 20.52% |
| | Hydro Gasoline (v %) | 25.14% | 25.43% |
| | Isomerate (v %) | 41.32% | 40.32% |
| | Reformate (v %) | 9.20% | 9.03% |
| | MTBE (v %) | 0.65% | 0.54% |
| | Toluene (v %) | 4.05% | 4.16% |
| | SUM | 100% | 100% |
| V97# Gasoline | Etherify Gasoline(v %) | 20.65% | 21.29% |
| | Hydro Gasoline (v %) | 18.81% | 18.08% |
| | Isomerate (v %) | 30.91% | 30.96% |
| | Reformate (v %) | 16.36% | 16.45% |
| | MTBE (v %) | 10.25% | 10.37% |
| | Toluene (v %) | 3.02% | 2.85% |
| | SUM | 100% | 100% |

As can be seen in the example comparison shown in Table 4, using the recipe optimization (RO) in accordance with the method, the remaining component mass balance after blending is less compared to blending using currently known methods of determining the blending ratio. The recipe optimization (RO) in accordance with the method is therefore more successful at minimizing the remaining component mass balance, which was the optimizing function chosen for this example.

2) Predicted Profit/Cost of Blending Operation or the Optimized Target Value:

Table 4 shows comparisons between the results with and without using the recipe optimization (RO) in accordance with the method.

3) Predicted Properties of Products after Blending:

Tables 5 and 6 below give a comparison of the results with and without using the recipe optimization (RO) in accordance with the method, respectively.

TABLE 5

PREDICTED BLENDING PRODUCT QUALITY WITHOUT USING RECIPE OPTIMIZATION

| No. | Product | Sulfur, ppm | RON | OLV, v % | BNZ, v % | OXY, wt % | ARO, v % |
|---|---|---|---|---|---|---|---|
| 1 | V93# Gasoline | 9.69 | 93.20 | 12.47 | 0.24 | 0.12 | 24.57 |
| 2 | V97# Gasoline | 9.85 | 97.28 | 12.04 | 0.22 | 1.86 | 26.05 |

TABLE 6

PREDICTED BLENDING PRODUCT QUALITY WITHOUT USING RECIPE OPTIMIZATION

| No. | Product | Sulfur, ppm | RON | OLV, v % | BNZ, v % | OXY, wt % | ARO, v % |
|---|---|---|---|---|---|---|---|
| 1 | V93# Gasoline | 9.99 | 93.28 | 12.91 | 0.24 | 0.10 | 24.70 |
| 2 | V97# Gasoline | 9.99 | 97.28 | 12.22 | 0.22 | 1.89 | 25.58 |

The recipe optimization (RO) in accordance with the method described above thus will allow users to foresee the quality of target product based on the given component property, blending recipe, heel property in target tank and predefined dedicate product oil blending rules, and search the optimal component blending recipe according to the specified optimization target, without providing the initial blending ratio. Overall, the benefits of applying this recipe optimization system may include, but are not limited to: 1) higher reliability of recipe blending operation, 2) optimizing of operation targets; 3) taking into consideration the consumption balance; and 4) obtaining the optimal recipe without having to provide an initial recipe data.

The above described examples demonstrate that the recipe optimization in accordance with the method will provide higher reliability of recipe blending operation with less dependence on a user's skill level. Users are allowed to get the final recipe for the target product oil property blending with significantly reduced operation time, greater improvement in the efficiency of blending operation and avoiding the need for re-blending by predicting the target product quality with high accuracy.

The above described examples demonstrate that the recipe optimization in accordance with the method will also provide optimizing of operation targets, such as maximizing overall economic profit, maximizing consumption of certain component, etc. while strictly meeting product specifications and other constraints.

The above described examples demonstrate that the recipe optimization in accordance with the method will also allow, taking into consideration a consumption balance of each component and the upstream refinery unit loading constraints, users to choose to minimize the remaining balance for certain blend components or all components, which links to the known specific upstream refinery unit loading constraints.

The above described examples demonstrate that the recipe optimization in accordance with the method will also provide obtaining the optimal recipe without having to provide an initial recipe data. For many new plants, or where a new specification of product oil or new component oil is introduced, there is no existing recipe to refer to, such that a user would spend a longer time to get the proper blending recipe using prior art methods, whereas by using the present invention, a user is able to arrive proper recipe quickly without an existing recipe to refer to.

It should be noted that in the recipe optimization in accordance with the method of the above examples, all the inputs, the boundary conditions for all constraints, the objective functions and the algorithm configuration parameters are changeable. The blending properties and rules may be different from those used or described in the above example.

Whilst there has been described in the foregoing description exemplary embodiments of the present invention, it will be understood by those skilled in the technology concerned that many variations in details of design, construction and/or operation may be made without departing from the present invention. For example, while different grades of gasoline blending have been described in the given example above, the present invention of recipe optimization using the recipe optimization in accordance with the method of the above examples can be applied for different product oil blending and crude oil blending applications. For crude oil blending, the blending rules for crude would be required, such as sulfur content, true boiling point (TBP), specific gravity, and so on, as would be appropriate.

The recipe optimizer could be enhanced further by working together with production scheduling and management system to schedule the production rate of each component from the refinery plant and coordinate with the blending operation and demand.

The systems and methods in the above-described embodiments may be deployed in part or in whole through a machine that executes computer software, software components, program codes, and/or instructions on one or more processors. The one or more processors may be part of a general-purpose computer, a server, a cloud server, a client, network infrastructure, mobile computing platform, stationary computing platform, or other computing platform. One or more processors may be any kind of computational or processing device or devices which are capable of executing program instructions, codes, binary instructions and the like. The one or more processors may be or include a signal processor, digital processor, embedded processor, microprocessor or any variants such as a co-processor, for example, math co-processor, graphic co-processor, communication co-processor and the like that may directly or indirectly facilitate execution of program codes or program instructions stored thereon. In addition, the one or more processors may enable execution of multiple programs, threads, and codes. The threads may be executed simultaneously to enhance the performance of the one or more processors and to facilitate simultaneous operations of the application. Program codes, program instructions and the like described herein may be implemented in one or more threads. The one or more processors may include memory that stores codes, instructions and programs as described herein. The processor may access a non-transitory processor-readable storage medium through an interface that may store codes, instructions and programs as described herein and elsewhere. The non-transitory processor-readable storage medium associated with the processor for storing programs, codes, program instructions or other type of instructions capable of being executed by the computing or processing device may include but may not be limited to one or more of a memory, hard disk, flash drive, RAM, ROM, CD-ROM, DVD, cache and the like.

A processor may include one or more cores that may enhance speed and performance of a multiprocessor. In some embodiments, the process may be a dual core processor, quad core processors, other chip-level multiprocessor and the like that combine two or more independent cores.

The methods and systems described herein may be deployed in part or in whole through a machine that executes computer software on a server, client, firewall, gateway, hub, router, or other such computer and/or networking hardware.

The software program may be associated with one or more client that may include a file client, print client, domain client, internet client, intranet client and other variants such as secondary client, host client, distributed client and the like. The client may include one or more of memories, processors, computer readable media, storage media, physical and virtual ports, communication devices, and interfaces capable of accessing other clients, servers, machines, and devices through a wired or a wireless medium, and the like. The programs or codes as described herein may be executed by the client. In addition, other devices required for execution of methods as described in this application may be considered as a part of the infrastructure associated with the client. The client may provide an interface to other devices including servers, other clients, printers, database servers, print servers, file servers, communication servers, distributed servers and the like. This coupling and/or connection may facilitate remote execution of program across the network. The networking of some or all of these devices may facilitate parallel processing of a program or method at one or more location. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The software program may be associated with one or more servers that may include a file server, print server, domain server, internet server, intranet server and other variants such as secondary server, host server, distributed server and the like. The server may include one or more of memories, processors, computer readable media, storage media, physical and virtual ports, communication devices, and interfaces capable of accessing other servers, clients, machines, and devices through a wired or a wireless medium, and the like. The methods, programs or codes as described herein may be executed by the server. In addition, other devices required for execution of methods as described in this application may be considered as a part of the infrastructure associated with the server. The server may provide an interface to other devices including clients, other servers, printers, database servers, print servers, file servers, communication servers, distributed servers, social networks, and the like. This coupling and/or connection may facilitate remote execution of program across the network. The networking of some or all of these devices may facilitate parallel processing of a program or method at one or more locations. Any of the devices attached to the server through an interface may include at least one storage medium capable of storing programs, codes and/or instructions. A central repository may provide program instructions to be executed on different devices. In this implementation, the remote repository may act as a storage medium for program codes, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing devices associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory, for example, USB sticks or keys, floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The modules, engines, components, and elements described herein, including in flow charts and block diagrams throughout the figures, imply logical boundaries between the modules, engines, components, and elements. However, according to software or hardware engineering practices, the modules, engines, components, and elements and the functions thereof may be implemented on one or more processors, computers, machines through computer executable media, which are capable of executing program instructions stored thereon as a monolithic software structure, as standalone software modules, or as modules that employ external routines, codes, services, or any combination of these, and all such implementations may be within the scope of the present disclosure. Examples of such machines may include, but is not limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, processor-embedded eyewear and the like. Furthermore, the modules, engines, components, and elements in the flow chart and block diagrams or any other logical component may be implemented on one or more machines, computers or processors capable of executing program instructions. Whereas the foregoing descriptions and drawings to which the descriptions have been referred set forth some functional aspects of the disclosed systems, no particular arrangement of software for implementing these functional aspects should be inferred from these descriptions unless explicitly stated or otherwise clear from the context. It will also be appreciated that the various steps identified and described above may be varied, and that the order of steps may be adapted to particular applications of the techniques disclosed herein. All such variations and modifications are intended to fall within the scope of this disclosure. The descriptions of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. An optimization system comprising:
   one or more processors;
   a recipe optimizer configured to randomly distribute solutions within predefined upper and lower limits of i) acceptable ranges in volumes of feed tanks and final product tanks; and ii) acceptable ranges in properties of an oil product, to generate random solutions including a random blending ratio of blending components for at least a product;
   a loop search engine configured to perform a loop search based on the random solutions, and to generate a first optimized blending ratio; and
   a local search engine configured to perform a local search based on the first optimized blending ratio, and to generate a second optimized blending ratio,
   wherein the loop search engine and the local search engine are implemented on the one or more processors.

2. An optimization system comprising:
   one or more processors;
   an initialization module configured to create a random blending ratio of blending components automatically;
   a loop search engine configured to perform a loop search based on the random blending ratio of blending components for at least a product, and to generate a first optimized blending ratio; and
   a local search engine configured to perform a local search based on the first optimized blending ratio, and to generate a second optimized blending ratio; and
   wherein the initialization module, the loop search engine and the local search engine are implemented on the one or more processors.

3. The optimization system of claim 2, wherein the loop search engine and the local search engine are configured to reiterate the loop search and the local search cyclically.

4. The optimization system of claim 3, wherein the loop search comprises a genetic algorithm loop search, and the local search comprises a Nelder-Mead simplex method search.

5. The optimization system of claim 2, further comprising:
   a generation counter module configured to count a generation number every time the loop search engine and the local search engine have performed the loop search and the local search, respectively,
   wherein the generation counter module is implemented on the one or more processors,
   wherein the loop search engine and the local search engine are configured to reiterate the loop search and the local search cyclically until the generation number counted by the generation counter module reaches a predetermined number, and
   wherein the loop search comprises a genetic algorithm loop search, and the local search comprises a Nelder-Mead simplex method search.

6. The optimization system of claim 2, wherein the initialization module is configured to create the random blending ratio, based on at least:
   an optimization target;
   configuration parameters of the loop search and the local search; and
   a set of boundary conditions.

7. The optimization system of claim 6, wherein the set of boundary conditions comprises:
   a specification of a product, the product being a blend of a plurality of blending components;
   an available amount of each of the blending components; and
   relevant properties of each of the blending components.

8. The optimization system of claim 7, wherein the specification of the product includes at least one of: sulfur content, research octane number, motor octane number, Reid vapour pressure, flash point, viscosity, olefin, benzene, oxygen, aromatics, boiling point, true specific gravity, and price of each product.

9. The optimization system of claim 8, wherein the relevant properties include at least one of: sulfur content, research octane number, motor octane number, Reid vapour pressure, flash point, viscosity, olefin, benzene, oxygen, aromatics, boiling point, true specific gravity, and cost of each of the blending components.

10. The optimization system of claim 6, wherein the optimization target includes an optimization of an objective function configured to:
    reduce a total cost of all the blending components to be used;
    increase a total profit of all the products together;
    reduce a total remaining mass balance of each blending component; and
    increase throughput of at least one of the products.

11. The optimization system of claim 2, further comprising:
    a user interface configured to display the second optimized blending ratio on a display screen.

12. The optimization system of claim 2, wherein the loop search engine comprises a genetic algorithm loop search engine, and wherein the local search engine comprises a Nelder-Mead simplex method search engine.

13. The optimization system of claim 2, further comprising:
- a memory device accessible by the one or more processor, the memory device stores a set of program components that, when executed by the one or more processor, cause the processor to act as the loop search and the local search engine.

14. The optimization system of claim 13, wherein the memory device stores: a set of information, the set of information comprising:
- a plurality of predefined boundary conditions;
- a plurality of minimized objective functions;
- a plurality of maximized objective functions, which are the reciprocals of the minimized objective functions; and
- a plurality of configuration parameters for a genetic algorithm loop search and a Nelder-Mead simplex method for the loop search and the local search engine, respectively.

15. The optimization system of claim 2, wherein the one or more processor is programmed to implement the loop search engine and the local search engine.

16. An optimization system comprising:
- one or more processors;
- a loop search engine configured to perform a loop search based on a random blending ratio of blending components for at least a product, and to generate a first optimized blending ratio;
- a local search engine configured to perform a local search based on the first optimized blending ratio, and to generate a second optimized blending ratio; and
- a user interface configured to display the second optimized blending ratio on a display screen,
- wherein the user interface is configured to receive to entry of at least:
- an optimization target;
- configuration parameters of the loop search and the local search; and
- a set of boundary conditions.

17. The optimization system of claim 16, further comprising:
- an initialization module configured to create the random blending ratio based on at least:
- the optimization target,
- the configuration parameters of the loop search and the local search, and
- the set of boundary conditions.

18. The optimization system of claim 17, wherein the set of boundary conditions comprises:
- a specification of a product which is a blend of a plurality of blending components;
- an available amount of each of the blending components; and
- relevant properties of each of the blending components.

19. The optimization system of claim 18, wherein the optimization target includes an optimization of an objective function configured to:
- reduce a total cost of all the blending components to be used;
- increase a total profit of all the products together;
- reduce a total remaining mass balance of each blending component; and
- increase throughput of at least one of the products.

20. The optimization system of claim 16, wherein the user interface is configured to receive an entry of information of an existing volume of each product in its product tank.

21. A computer-implemented method of optimizing a blending ratio of blending components for at least a product, the method comprising:
- randomly distributing solutions within predefined upper and lower limits of i) acceptable ranges in volumes of feed tanks and final product tanks; and ii) acceptable ranges in properties of an oil product, to generate random solutions including a random blending ratio of blending components for at least a product;
- performing a loop search based on the random solutions including a random blending ratio of blending components for at least a product, to generate a first optimized blending ratio; and
- performing a local search based on the first optimized blending ratio, to generate a second optimized blending ratio,
- wherein randomly distributing the solutions, the loop search and the local search are performed using one or more processors.

22. A computer-implemented method of optimizing a blending ratio of blending components for at least a product, the computer-implemented method comprising:
- creating a random blending ratio of blending components automatically for initialization, based on at least: an optimization target; configuration parameters for a loop search and a local search; and a set of boundary conditions;
- performing the loop search based on the random blending ratio of blending components for at least a product, to generate a first optimized blending ratio; and
- performing the local search based on the first optimized blending ratio, to generate a second optimized blending ratio;
- wherein creating the random blending ratio, performing the loop search and performing the local search are made using one or more processors, and
- wherein the set of boundary conditions comprises:
- a specification of a product, the product being a blend of a plurality of blending components;
- an available amount of each of the blending components; and
- relevant properties of each of the blending components.

23. The method of claim 22, further comprising:
reiterating the loop search and the local search cyclically.

24. The method of claim 23, wherein the loop search comprises a genetic algorithm loop search, and the local search comprises a Nelder-Mead simplex method search.

25. The method of claim 22, further comprising:
- counting a generation number every time the loop search and the local search have been performed, wherein the counting operation is implemented using the one or more processors; and
- reiterating the loop search and the local search cyclically until the generation number counted reaches a predetermined number,
- wherein the loop search comprises a genetic algorithm loop search, and the local search comprises a Nelder-Mead simplex method search.

26. A non-transitory computer-readable storage medium storing a set of information, the set of information comprising:
- a plurality of predefined boundary conditions;
- a plurality of minimized objective functions;
- a plurality of maximized objective functions, which are the reciprocals of the minimized objective functions;

a plurality of configuration parameters for a genetic algorithm loop search and a Nelder-Mead simplex method, wherein the plurality of predefined boundary conditions comprises:

a plurality of predefined oil blending rules;

a plurality of configurable number of component tank and product tank;

a plurality of configurable minimum and maximum values of blending ratio parameters;

a plurality of configurable minimum and maximum values of product oil property specifications;

a plurality of configurable minimum and maximum values of volumes of component tank and product tank;

a plurality of configurable remaining volume of product tank;

a plurality of configurable cost of component oil and price of product oil; and a plurality of configurable penalty coefficients for constraints to get constraint conditions as constraint violation term.

27. An article of manufacture including a non-transitory computer-readable medium having instructions stored thereon that, when executed by a computing device, cause said computing device to perform operations comprising:

creating a random blending ratio automatically for initialization, based on at least: an optimization target; configuration parameters for a loop search and a local search; and a set of boundary conditions;

performing the loop search based on the random blending ratio of blending components for at least a product, to generate a first optimized blending ratio; and performing the local search based on the first optimized blending ratio, to generate a second optimized blending ratio.

28. A computer-implemented method of creating a random blending ratio for optimizing a blending ratio of blending components for at least a product, the computer-implemented method comprising:

receiving, by one or more processors, entry of at least an optimization target, configuration parameters for a loop search and a local search, and a set of boundary conditions which are stored on a non-transitory computer-readable storage medium; and creating, by the one or more processors, a random blending ratio based on at least the optimization target, the configuration parameters, and the set of boundary conditions, wherein the set of boundary conditions comprises:

a specification of a product, the product being a blend of a plurality of blending components;

an available amount of each of the blending components; and relevant properties of each of the blending components.

29. A computer-implemented method of creating a random blending ratio for optimizing a blending ratio of blending components for at least a product, the computer-implemented method comprising:

receiving, by one or more processors, entry of at least an optimization target, configuration parameters for a loop search and a local search, and a set of boundary conditions which are stored on a non-transitory computer-readable storage medium; and creating, by the one or more processors, a random blending ratio based on at least the optimization target, the configuration parameters, and the set of boundary conditions, wherein the optimization target includes an optimization of an objective function configured to:

reduce a total cost of all the blending components to be used;

increase a total profit of all the products together;

reduce a total remaining mass balance of each blending component; and increase throughput of at least one of the products.

* * * * *